United States Patent [19]

Letsinger

[11] Patent Number: 4,958,013

[45] Date of Patent: Sep. 18, 1990

[54] CHOLESTERYL MODIFIED OLIGONUCLEOTIDES

[75] Inventor: Robert L. Letsinger, Wilmette, Ill.

[73] Assignee: Northwestern University, Evanston, Ill.

[21] Appl. No.: 362,200

[22] Filed: Jun. 6, 1989

[51] Int. Cl.$^5$ ............................................. C07H 21/00
[52] U.S. Cl. ......................................... 536/27; 536/5; 536/28; 536/29
[58] Field of Search ......................... 536/5, 27, 28, 29; 514/49, 50

[56] References Cited

U.S. PATENT DOCUMENTS

| | | | |
|---|---|---|---|
| 4,283,394 | 8/1981 | West et al. | 536/5 |
| 4,458,066 | 7/1984 | Caruthers et al. | 536/27 |
| 4,728,730 | 3/1988 | Frey et al. | 536/28 |

*Primary Examiner*—John W. Rollins
*Assistant Examiner*—James O. Wilson
*Attorney, Agent, or Firm*—Tilton, Fallon, Lungmus & Chestnut

[57] ABSTRACT

Oligonucleotides modified at their backbones by the attachment of cholesteryl are described. The modified oligonucleotides anchor in the cell membrane to serve as a probe and to provide therapeutic activity.

3 Claims, No Drawings

CHOLESTERYL MODIFIED OLIGONUCLEOTIDES

GRANT REFERENCE

This invention was developed with support provided by the National Cooperative Drug Discovery Group for the Treatment of AIDS, Grant U01 A124846 from the National Cancer Institute of Allergy and Infectious Diseases and by Grant 5R37GM10265 from the National Institute of General Medical Science.

FIELD OF INVENTION, BACKGROUND AND PRIOR ART

This invention relates to oligonucleotides modified by a pendant cholesteryl group. More particularly, the present invention is related to a cholesteryl modified oligonucleotide and a method of using the modified oligonucleotide as an antiviral agent.

The pioneering work of Zamecnik and Stephenson, Proc. Natl. Acad., 75:280-284 (1978), on antiviral activity of oligonucleotides and Miller and Ts'o, on the chemistry and biochemistry of non-ionic analogues (Barrett, et al., Biochem., 13:4898-5 (1974) and Jayaraman, et al. Proc. Natl. Acad Sci. U.S.A., 78:1537-1541 (1981)) has stimulated extensive research directed the therapeutic potential of nucleotide polymers. Oligonucleotide analogues with methylphosphonate, Miller, et al., Biochemie, 67: 769-776 (1985), Agris, et al., Biochem., 25:6268-6275 (1986), Smith, et al., Proc. Natl. Acad. Sci. U.S.A., 83:2787-2791 (1986), and Sarin, et al., Proc. Natl. Acad. Sci. U.S.A., 85:7448-7451 (1988); phosphorothioate, Matsukura, et al., Proc. Natl. Acad. Sci. U.S.A., 84:7706-7710 (1987) and Agrawal, et al., Proc. Natl. Acad. Sci. U.S.A., 85:7079-7083 (1988); and phosphoramidate, Agrawal, et al., Proc. Natl. Acad. Sci. U.S.A., 85:7079-7083 (1988), backbones as well as natural type oligonucleotides Zamecnik, et al., Proc. Natl. Acad. Sci. U.S.A., 83:4143-4146 (1986), and a polylysine conjugate, Goodchild, et al., Proc. Natl. Acad. Sci. U.S.A., 85:5507-5511 (1988), have now been reported to inhibit viral replication in cell culture. The viruses studied in this context include Rous sarcoma virus, Zamecnik and Stephenson, Proc. Natl. Acad., 75:280-284 (1978); simian virus, Miller, et al., Biochemie, 67: 769-776 (1985); vesicular stomatitis virus, Agris, et al., Biochem., 25:6268-6275 (1986) and Lemaitre, et al., Proc. Natl. Acad. Sci. U.S.A., 84:648-652 (1987); human immunodeficiency virus (HIV), Sarin, et al., Proc. Natl. Acad. Sci. U.S.A., 85:7448-7451 (1988), Matsukura, et al., Proc. Natl. Acad. Sci. U.S.A., 84:7706-7710 (1987), Agrawal, et al., Proc. Natl. Acad. Sci. U.S.A., 85:7079-7083 (1988), Zamecnik, et al., Proc. Natl. Acad. Sci. U.S.A., 83:4143-4146 (1986), and Goodchild, et al., Proc. Natl. Acad. Sci. U.S.A., 85:5507-5511 (1988); herpes simplex virus, Smith, et al., Proc. Natl. Acad. Sci. U.S.A., 83:2787-2791 (1986); and influenza virus, Zerial, et al., Nuc. Acids. Res., 15:9909-9919 (1987).

The concept underlying this work is that an oligonucleotide complementary to a unique segment of a viral genome, or an RNA derived from it, may selectively disrupt processes dependent on that segment by hybridization. This rationale is supported by a variety of experiments with cell free systems or with cells to which "antisense" polynucleotides have been inserted by microinjection or transfection, C. A. & Cohen, J. S., Cancer Res., 48:2659-2668 (1988). However, the actual mechanisms by which oligonucleotides and their analogs function as inhibitors in cell cultures are still far from clear. In particular, little is known about the interaction of the oligomers with cell membranes or the locus of their reactions within cells. It appears that non-ionic oligomers, such as the methyl phosphonate analogues diffuse passively through cell membranes.

S. E. Clare has synthesized oligonucleotides possessing one or more 2,2,2-trichloral-1,1-dimethylethyl (TDCME, lipophilic) group at the phosphorous atom in the chain and show that this group on one strand with proper stereochemistry can inhibit cleavage of the opposite strand by a restriction endonuclease and that the same group on a template will inhibit synthesis of the complementary strand by the Klenow enzyme. S. E. Clare also demonstrated a single modification 5' to dGNAd(CG) octamer by TDCME group prevents the B to Z conformational transition. S. E. Clare, Ph.D. Dissertation, Northwestern University, Evanston, Ill. (1987).

The present invention is related to a family of oligonucleotides modified at the backbone so that the oligonucleotide may anchor at the cell membrane to provide antiviral effects. The present invention describes a family of oligonucleotides with a modification designed to anchor the oligomer, at least transiently at the cell membrane, to inhibit HIV-1 in cell culture. Fatty substances have been selected as an anchor for the oligonucleotide, and without being limitative, cholesteryl has been selected as the preferred anchor since it is highly hydrophobic and cell membranes have an abundance of this steroid.

The cholesteryl is a large lipophilic group, much larger than the TDCME group. In principle, such pendent groups, when linked covalently to the internucleotide phosphorous atoms, have potential as lipophilic centers to enhance the interaction with membranes, to alter partitioning of oligonucleotides within cells, to inhibit certain enzymatic reactions and to influence the stability of hybrids joined with natural polynucleotides. Cholesteryl, is a component of many biological membranes and interacts with other lipids. The AIDS virus, HIV, is distinguished by an unusually high cholesteryl content in the lipid membrane. Early model studies by Finean, Experientia, 9:17-19 (1985), suggested that the cholesteryl molecule is capable of formation of a stabilizing complex with the phospholipid molecule. The hydrocarbon chain of the cholesteryl is bound to the parallel portion of the phospholipid chain by Van DeWall forces. Recent studies employing a variety of techniques indicated that the major forces may involve the hydrophobic portion of the lipid molecules. Therefore, cholesteryl is a preferred modifying group for oligonucleotide interaction with cells.

SUMMARY OF THE INVENTION

The invention is concerned with oligonucleotides that are modified to anchor the oligomer at the cell membrane so that the oligonucleotide may serve as a probe and provide therapeutic activity.

The novel oligonucleotide compounds of the present invention can be represented by the following structural formula:

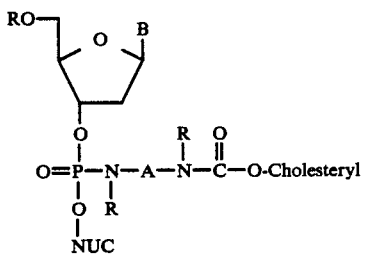

Formula I wherein A=aliphatic alkyl or branched aliphatic alkyl or a heteroatom containing an alkyl (branched) chain of 2 to 18 carbon atoms, preferably $CH_2$, R=H and lower alkyl up to 12 carbon atoms, preferably methyl; NUC refers to an oligonucleotide which may be a deoxyribonucleoside or a ribonucleoside. Preferred nucleosides are thymidine, deoxyadenosine, deoxyguanosine and deoxycytidine. The nucleosides are connected respectively to the phosphorous through their 3' and 5' oxygens, B is a purine or pyrimidine base (such as Thy, Cyt, Gua, Ade).

Cholesteryl has been selected as the preferred anchor because it is highly hydrophilic and found in cell membranes. The cholesteryl modified oligonucleotides of the present invention have been found to inhibit HIV-1 in cell culture. The location of the insertion of the cholesteryl anchor on the oligonucleotide may be varied and is not dependent on sequence.

DETAILED DESCRIPTION OF THE INVENTION

The novel compounds of Formula I can be prepared by convenient procedures for introducing a cholesteryl group at any desired internucleoside phosphorous in the course of synthesizing an oligonucleotide. The cholesteryl may be linked to an oligonucleotide as a substituent at either the 3'-O or 5'-O terminus.

Processes for preparing the novel compounds of Formula I are generally described by equations A and B.

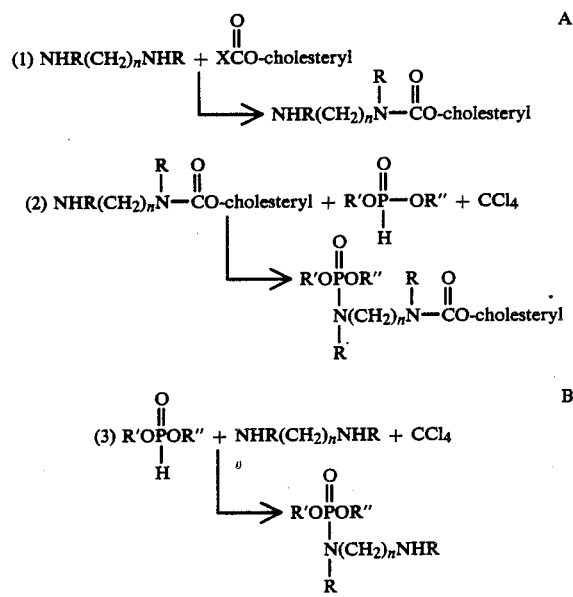

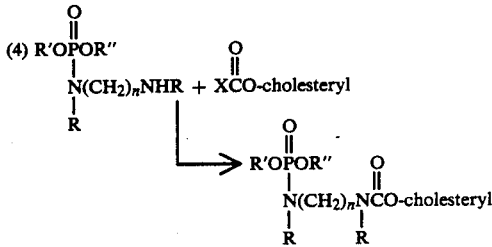

In the reactions, $X=Cl^-$ and p-nitrophenoxy, n=2 and 6, and R=H and methyl. The reactions for linking the amines to phosphorous are based on the general procedure of Froehler, B. C., *Tet. Lett.*, 27:5575–5578 (1986) for generating P-N bonds in oligonucleotide derivatives. The article is incorporated by reference.

Equation A avoids side reactions involving condensation at both nitrogen atoms of the diamine to form bisphosphoramidates. Procedures for preparing fifteen compounds of Table I with the cholesteryl anchor are described as follows: phosphodiester links were formed by cyanoethyl phosphoramidite chemistry described in the standard synthesis protocol provided by the manufacturer of the synthesizer, for example, Biosearch 8600, Biosearch, Inc., San Raphael, Calif. Chain extension by hydrogen phosphonate chemistry is described by Froehler, et al., *Tet. Lett.*, 27:469–472 (1986) and Froehler, et al., *Nuc. Acids. Res.*, 14:5399–5407 (1986). Phosphorothioate functional groups are added by the procedure of Froehler, et al., *Tet. Lett.*, 27:5575–5578 (1986).

Experimental Procedures 2-(Cholesteryloxycarbonylamino)ethylamine.

Cholesteryl chloroformate (2 g) in dichloromethane (6 ml) was added dropwise to a solution of ethylenediamine (2.5 ml) in dichloromethane (6 ml) and pyridine (6 ml). The mixture was stirred for two hours; then the solvent was removed under vacuum and the residue was partitioned between water (150 ml) and dichloromethane (150 ml). The organic layer was washed with water, dried ($Na_2SO_4$), and concentrated to give the title compound; 1.6 g (76%), mp 149–155 degrees Centigrade. Recrystallization from cyclohexane afforded crystals melting at 152–155 degrees Centigrade; Rf on silica ($CHCl_3$/MeOH, 1/1 v/v) 0.15; positive ninhydrin test. Anal. Calcd for $C_{30}H_{52}N_2O_2$; C, 76.22; H, 11.09; N, 5.93. Found: C, 75.96; H, 11.10; N, 5.86.

Preparation of Cholesteryl-Modified Dinucleoside Monophosphate on CPG Support.

Internucleoside cholesteryl side chains were linked to phosphorous via phosphoramidate bonds (adaption of procedure of Froehler). The preparation of d-DMT-ibG$_c$ibG-CPG is representative. A sample of DMT-ibG linked through the 3'-O to a controlled-pore-glass support (Biosearch) (250 mg. 8 micro moles of DMT-ibG) was placed in a Glencoe Gas-tight syringe (10 ml) equipped with a plug of glass wool at the inlet. Reactions and washings were carried out by drawing in an ejecting the desired solutions. Thus, the DMT groups was removed with dichloroacetic acid (2.5% in $CH_2Cl_2$); the support was washed repeatedly with $C_5H_5$/$CH_3CN$ (1/4), coupling was effected by drawing in together DMT-ibG-hydrogen phosphonate (80 mg, 0.1 mmol, in 1.2 ml $CH_3CN/C_5H_5$) and trimethylacetyl chloride (65 micro L, 0.5 micro moles, in 1.2 ml CH$_3$CN/C$_5$H$_5$, 1/1 v/v; 2 minutes), and the support was washed well with CH$_3$CN/C$_5$H$_5$. A solution of cholesteryloxycarbonylaminoethylamine (250 mg, 0.5 mmol) in CCl$_4$ (5 ml) and C$_5$H$_5$ (2 ml) was then drawn into the syringe and after 0.5 hours, the solution was ejected and the solid was washed well with CH$_3$CN. Appropriate portions were then transferred to a cartridge for extension by machine synthesis (Biosearch 8600 Synthesizer) or to a syringe for manual synthesis.

Chain Extension. The oligonucleotide chains were extended by conventional phosphoramidite chemistry in constructing phosphodiester links and by hydrogen phosphonate chemistry in building the phosphorothioate derivatives. The manual procedure used in adding a thymidine unit to DMT-ibG*C-CPG in synthesizing compound 2 in Table 1 is representative of one synthetic cycle utilizing a phosphoramidite reagent.

The DMT(G*G) loaded CPG (30 mg, 1 micro mole) was poured into a 1.0 ml Glenco Gas tight syringe with a glass wool plug at the inlet. Washes were effected by drawing up the desired amount of the reagent, resuspending the support by brief hand agitation, and ejecting the solution. The DMT protecting group was removed by washing with DCA/CH$_2$CH$_2$Cl$_2$ (2.5/100 v/v, 5.0 ml), and orange effluents were pooled for subsequent spectroscopy (447 nm) and calculation of the coupling efficiency. The support was washed successively with C$_5$H$_5$N/CH$_3$CN ($\frac{1}{4}$, v/v, 1×0.5 ml), and CH$_3$CN (2×0.5 ml). Any unreacted 5'-OH groups were capped by drawing DMAP in C$_5$H$_5$N/THF (0.3M, 1/15, v.v, 0.5 ml) into the syringe, followed immediately by Ac$_2$O/THF (0.6M, 0.5 ml). The mixture was agitated for one minute, capping agents were ejected from the syringe, and the support was washed with C$_5$H$_5$N/CH$_3$CN ($\frac{1}{4}$, v/v, 1×5.0 ml) and CH$_3$CN (1×0.5 ml). The phosphite internucleoside linkage was oxidized to the phosphotriester linkage with I$_2$ in C$_5$H$_5$N/THF/H$_2$O (0.1M I$_2$, 18/80/2, v/v/v, 0.5 ml) for two minutes. The oxidant was ejected, and the support was washed with C$_5$H$_5$N/CH$_3$CN ($\frac{1}{4}$, v/v, 3×1.5 ml) and CH$_3$CN (3×1.5 ml) to complete one synthetic cycle.

For chain extension by hydrogen phosphonate chemistry the DMT-ibG*ibG-cpg (1 micro mole loaded dimer) was detritylate as in the previous case. A solution of the DMT-nucleoside hydrogen phosphonate (10 mg, about 15 micro moles, in CH$_3$CN/C$_5$H$_5$N (1/1, v/v, 0.3 ml) was drawn into the syringe, which was agitated for two minutes. The coupling agents were ejected from the syringe, and the support washed with C$_5$H$_5$N/CH$_3$CN (1/1, v/v, 0.5 ml), and CH$_3$CN (3×0.5 ml) to complete one synthetic cycle. Additional couplings were performed by returning to the initial wash and repeating the cycle. Oxidation following the final coupling step was performed by treatment with 0.1M sulfur in CCl$_4$/Et$_3$N (9/1, v/v) at room temperature for two hours. After all nucleotide units had been added, the hydrogen phosphonate links were converted to phosphorothioates by drawing into the syringe at 0.1M solution of sulfur in CCl$_4$/Et$_3$N (9/1, v/v) at room temperature (two hours reaction). Procedures for machine syntheses were similar.

Isolation of Oligonucleotides

The oligomers were removed from the syringe or the synthesizer and warmed in a capped vessel with concentrated NH$_4$OH at 55 degrees Centigrade for five hours. The aqueous solution was then removed and concentrated under reduced pressure to give the crude oligonucleotide. This substance was chromatographed on a C-18 column and the band corresponding to the desired target oligomer was collected and lyophilized.

TABLE 1

| | Properties of Oligonucleotides | HPLC$^a$ min | TLC$^b$ R$_f$ | PAGE$^c$ R$_m$ | T$_m^d$ °C. |
|---|---|---|---|---|---|
| compound | | | | | |
| 1 | ACACCCAATTCTGAAAATCC Cholesteryl Substituents | 12.2 | 0.26 | 0.64 | 60 |
| 2 | ACACCCAATTCTGAAAATG*G | 46.0 | 0.41 | 0.55 | 60 |
| 3 | ACTCCGAAAGATAAAG*G | 46.6 | 0.43 | 0.54 | — |
| 4 | A*CACCCAATTCTGAAAATC*G | 61.0 | 0.58 | $e$ | 52 |
| 5 | CAATTCTCAAAATG*G | 46.5 | 0.54 | 0.64 | 46.5 |
| 6 | A$_s$C$_s$A$_s$C$_s$C$_s$C$_s$A$_s$A$_s$T$_s$T$_s$C$_s$T$_s$G$_s$A$_s$A$_s$A$_s$A$_s$T$_s$G$_s$G | 16.5 | 0.59* | 0.67 | 44 |
| 7 | A$_s$C$_s$A$_s$C$_s$C$_s$C$_s$A$_s$A$_s$T$_s$T$_s$C$_s$T$_s$G$_s$A$_s$A$_s$A$_s$A$_s$T$_s$G*G | 40.2 | 0.61 | 0.64 | 47.5 |
| 8 | C$_s$A$_s$A$_s$T$_s$T$_s$C$_s$T$_s$G$_s$A$_s$A$_s$A$_s$A$_s$T$_s$G$_s$G | 17.3 | 0.47 | 0.67 | 29 |
| 9 | C$_s$A$_s$A$_s$T$_s$T$_s$C$_s$T$_s$G$_s$A$_s$A$_s$A$_s$A$_s$T$_s$G*G | 47.4 | 0.59 | 0.63 | 25 |
| 10 | C$_s$T$_s$G$_s$A$_s$A$_s$A$_s$A$_s$T$_s$G$_s$G | 15.6 | 0.52 | 0.76 | — |
| 11 | C$_s$T$_s$G$_s$A$_s$A$_s$A$_s$A$_s$T$_s$G*G | 49.6 | 0.56 | 0.62 | — |
| 12 | G$_s$A$_s$C$_s$T$_s$T$_s$T$_s$A$_s$G*G | 45 | 0.60 | 0.73 | — |
| 13 | C$_s$T$_s$G$_s$A$_s$T$_s$T$_s$T$_s$G*G | 45.2 | 0.59 | 0.76 | — |
| 14 | A$_s$A$_s$A$_s$A$_s$T$_s$G*G | 47.5 | 0.66 | 0.62 | — |
| 15 | T$_s$T$_s$T$_s$T$_s$T$_s$T$_s$T$_s$T$_s$T$_s$T$_s$T$_s$T$_s$T*T | 50.0 | 0.60 | 0.65 | 16 |

In formulas * represents O = P — NH(CH$_2$)$_2$NHCO$_2$ cholesteryl; s represents O = P — S$^-$, and + represents O = PNH(CH$_2$)$_3$N(CH$_3$)$_2$. Altered nucleotides in 7 are underlined.
$^a$Elution time, Hewlett-Packard RP-C18 column (10 cm); 0.1 M triethylammonium acetate (pH 7.0), 1%/min acetonitrile gradient starting at 0% acetonitrile; 0.5 ml/min flow rate.
$^b$Thin layer chromatography on Merck silicia plates with propanol/ammonium hydroxide/water, 55/10/35 v/v/v.
$^c$Polyacrylamide gel electrophoresis in 20% crosslinked gel at pH 8.0, R$_m$ is migration relative to bromophenol blue.
$^d$T$_m$ is the temperature at the midpoint for the maximum slope in a plot of A$_{260}$ versus temperature in 0.1 M aqueous NaCl, 0.01 M Tris buffer at pH 7.0; total nucleotide concentration (base units) in approximately 10$^{-4}$ M. In each case, the complement is a phosphodiester strand equal in length to the modified oligomer.
$^e$The sample appeared as a broad streak starting at R$_m$ 0.2. The complement for determination of T$_m$ was poly d(A).

Coupling efficiency introducing a cholesteryl fragment to the compounds of Table 1 exceeded 50%.

As noted, phosphodiester links were formed in compounds 2-5 by conventional cyanoethyl phosphoramidaite chemistry as described in the standard synthesis protocol provided by the manufacturer of the synthesizer, Biosearch, Inc., San Raphael, Calif. For compounds 6-15, the chains were extended by hydrogen phosphonate chemistry as described by Froehler, et al., Tet. Lett., 27:469-472 (1986) and Froehler, et al.,

*Nuc. Acids. Res.*, 14:5399–5407 (1986), the final oxidation with sulfur to generate the phosphorothioate groups.

The compounds were characterized by HPLC, TLC, PAGE, thermal disassociation curves for hybrids formed with complimentary strands and by UV and NMR spectroscopy. The NMR spectra exhibited the characteristic peaks for phosphodiester, phosphoramidate and phosphorothioate functional groups. A proton NMR spectrum of compound 2 shows the presence of the cholesteryl fragment. Further, the hydrophobic nature of the cholesteryl-oligonucleotides was shown by the HPLC data in Table 1. For example, the elution times for samples analyzed by a reverse phrase C-18 column increased from 14 to 46 to 61 minutes for the series 1 (control), 2(one) cholesteryl, and 4(two) cholesteryl, respectively. Susceptibility to nuclease degradation was examined with compound 2. In the presence of snake venom, phosphodiesterase, an alkaline phosphatase, compound 2 was completely hydrolyzed to the expected nucleosides and the fragment corresponding to the terminal G*G.

The data in Table 1 shows that the introduction of a single cholesteryl fragment at a terminal internucleoside position has only a minor effect on the stability of the hybrid duplex as measured by $T_m$ values when compound 1 is compared with 2; compound 6 compared with 7, and compound 8 compared with 9. Conversely, two cholesteryl substituents led to appreciable destabilization for the 20-mer compound, compare compound 4 with 1. The disassociation of complexes formed from equi-molar quantities in modified and unmodified complementary oligodeoxyribo-nucleotides were measured by changes in adsorbents in 260 nm as a function of temperature.

Additional compounds were made in accordance with Equation B, wherein $R=CH_3$, $N=6$, $X=-OC_6H_5MO_2$. The following compounds were prepared: 16, TTTTTTTTT#T; 17, T#TTTTTTTTT; 18, TTTT#TTTTTT; and 19, CGCG#AATTCGCG, where # is $O=P-N(CH_3)(CH_2)_6N(CH_3)CO_2$ cholesteryl. The procedures of Froehler, B. C., *Tet. Lett.*, 27:5575–5578 (1986) and Marcus-Sekura, et al., *Nuc. Acids. Res.*, 15:5749–5763 (1987) were followed in preparing phosphodiester links in compounds with internal modifications to avoid or minimize complications which could arise from the premature formation of phosphodiester groups in the course of the synthesis. As in the case of the derivatives of ethylenediamine, introduction of substituents at the terminal internucleoside links had little effect on $T_m$ values for the hybrids formed in complementary sequence ($T_m$ for 1:1 complexes with poly d(A) in 0.1M NaCl, pH 7: 28 degrees Centigrade for compound 16, 27 degrees Centigrade for compound 17 and 28 degrees Centigrade for parent $T_9T$). Conversely, modification of the centrally positioned internal link led to significant destabilization (21 degrees Centigrade $T_m$ for compound 18). The mobility of stereoisomers of compound 19 on HPCL differed sufficiently to permit separation of the isomers. The $T_m$ for the duplexes formed from these self-complementary modified strands (stererisomers of compound 15) were substantially lower than that for the parent duplex ($T_m$:40 degrees and 45 degrees Centigrade for the isomers as compared to 56 degrees Centigrade for CGCGAATTCGCG; 0.1M NaCl, pH 7.0).

The linking of cholesteryl to an oligonucleotide as a substituent at the 5'-O terminus is quite simple and can be shown by the following example.

Synthesis and characterization of cholesteryl-sTsGsG.

DMT(G) loaded CPG (88.2 mg, about 3 micro moles) was poured into 5 ml Glencoe gas tight syringe with a glass wool plug at the inlet. Washes were effected by drawing up the desired amount of the reagent, resuspending the support by brief hand agitation and ejecting the solution. The support was initially washed with $CH_3CN$ (4.5 ml×3) and $CH_2Cl_2$ (4.5 ml×2). The DMT projecting group was removed by washing with $DCA/CH_2Cl_2$ (2.5/100, v/v, 10 ml). All of the orange effluents were pooled for subsequent spectroscopy (448 nm) and calculation of the coupling efficiency.

The support was washed successively with pyricine/$CH_3CH$ (¼, v/v, 4.5 ml×3), $CH_3CN$ (4.5 ml×4) and dry $CH_3CN$ (4.5 ml×6). The H-phosphonate solution (for G and T - 36 mg, about 0.06 micro moles in dry $CH_3CH$/pyridine, 1/1, v/v, 2 ml); for cholesteryl H-phosphonate-42 mg, about 0.09 micro moles in dry $CH_3CN$/pyridine, ⅓, v/v, 2.0 ml) and trimethylacetyl chloride solution (0.03 ml, about 0.351 micro moles in trimethylactyl chloride solution (0.03 ml, about 0.351 micro moles in dry $CH_3CN$/pyridine, v/v, 2 ml) were drawn into the syringe, which was agitated for five minutes (but for 15 minutes for cholesteryl H-phosphonate coupling). After each coupling, the reagents were ejected from the syringe and the procedure was continued by returning to the initial wash steps.

Oxidation, following final coupling step and wash with dry $CH_3CN$ (4.5 ml×3), dry pyridine (4.5 ml×4) was performed with 0.1 58 in $CS_2Et_3N$(9/1, v/v, 5 ml) at room temperature for two hours. After that, the support was washed with $CS_2$/pyridine (1/1, v/v, 4.5 ml×2), $CH_3N$ (4.5 ml×3), dry $CH_3CN$ (4ml×3) and ether (5 ml×4). After drying the CPG-bound product was treated with 3.0 ml concentrated $NH_4OH$ at 55 degrees Centigrade for five hours. Upon removal of $NH_4OH$ by evaporation under reduced pressure, CPG support was removed by filtration; the filtrate freeze-dried overnight and the product redissolved in 2.0 ml $H_2O$. For UV spectroscopy, 10 micro liters of this solution were added to 990 micro liters of $H_2O$.

HPLC data indicated about 50% of the reaction mixture was the desired product. Spectroscopic methods also confirm the desired structure.

Compound of Formula I of the present invention can also be utilized in a method for hybridizing with a complementary sequence in a solution under conditions conducive to the hybridization. Typically, these conditions are controlled by the complementary sequence. The specific conditions needed for hybridization would be known to one skilled in the art familiar with the complementary sequence and environment for hybridization.

The present invention further comprises the method of modifying the backbone of an oligonucleotide by the attachment of a fatty substance, preferably cholesteryl so that it will anchor into the cell membrane so that the modified oligonucleotide will hybridize with the complementary sequence. By anchoring into the cell membrane, the oligonucleotide may provide diagnostic or therapeutic activity. For example, the oligonucleotide compound 1 of Table 1 is complementary to the splice acceptor for site at 5349–5368 in HIV-1 and has been shown to inhibit replication of this virus in MOLT-3 cells by Zerial, et al., *Nuc. Acids Res.*, 15:9909–9919 (1987) and Stein, et al., *Cancer Res.*, 48:2659–2668 (1988). The compounds shown in Table 1 are structural variations of the basic sequence of compound 1. Compounds 2–15 were designed to provide information on the antiviral properties of the cholesteryl modified oligonucleotides and, specifically, on the dependence of the antiviral activity on 1 (the number of cholesteryl fragments incorporated in the backbone chain), 2 (the nature of the main backbone section e.g. phosphodiester venus phosphorothioate links), 3 (the length of the oligonucleotide) and 4 (the sequence integrity of the oligonucleotide.

Samples of the oligomers were assayed in the following test:

Assays for HIV-1 Inhibition.

The inhibition of HIV-1 expression in H9 or MOLT-3 cells in the presence of antisense oligonucleotides was carried out by infecting $5 \times 10^5$ cells per ml with $2.5–5 \times 10^8$ virus particles of HIV-1 strains HTLV-IIIB or HTLV-IIIC. Infection with 500–1000 virus particles per cell represents a multiplicity of infection (MOI) of 0.5–1. HIV-1 infection of cells was carried out by simultaneous addition of virus and cholesteryl modified oligomers to the cells in culture. The cultures were incubated in culture medium containing RPMI 1640, 10% (v/v) fetal bovine serum, 2 mM gultamine, and 250 micro grams of gentamicin per ml, in a humidified atmosphere containing 5% $CO_2$ at 37 degrees Centigrade. After four days, the cells and supernatant were examined for the level of HIV-1 expression by measuring syncytia (MOLT-3 cells) and viral antigen expression as well as cell viability. The number of syncytia formed in MOLT-3 cells were counted after triturating the cells to obtain an even distribution of the syncytia in the culture. The average number of syncytia as obtained by counting several fields in duplicate cultures. Cell viability was measured in the presence of trypan blue, and the cells that excluded the dye were counted as viable cells. HIV-1 antigen expression was measured in cells fixed in methanol/acetone as described. Sarin, et al., *Biochem. Pharmacol.*, 34:4075–4078 (1985) and Sarin, et al., *J. Natl. Cancer Inst.*, 78:663–666 (1987). In brief, the cells were pelleted and then resuspended in phosphate-buffered saline (PBS) at a concentration of 106 cells per ml. The cells were spotted on toxoplasmosis slides, airdried, and fixed in methanol/acetone (1:1, v/v) for 15 minutes at room temperature. The slides were next incubated with 10% normal goat serum at room temperature for 30 minutes and washed with PBS four times. HIV-1 p24 or P17 monoclonal antibody was added to each well and the slides were incubated for 30 minutes in a humid chamber at 37 degrees Centigrade. The slides were then washed four times with PBS, incubated with fluorescein isothiocyanate-labeled goat anti-mouse IgG (Cappel Laboratories, Cochranville, Pa.) for 30 minutes at 37 degrees Centigrade, and then washed with PBS overnight. The slides were counterstained with Evan's blue, washed with PBS, mounted with 50% glycerol, and examined with a Zeiss fluorescence microscope. The percentages of cells fluorescing in the oligomer-treated and untreated cultures were compared. Inhibition of HIV-1 expression in the presence of oligomers was found to be similar in both the H9 and the MOLT-3 cells.

Inhibition of HIV-1 expression and H9 and MOLT-3 cells in the presence of cholesteryl modified oligonucleotides was carried out and results shown in Tables 2 and 3.

The data for the inhibition of formation of syncytia, an expression of HIV proteins P17, P24 and reverse transcriptase shown for compounds 1–5 in Table 2 and compounds 6–16 in Table 3. The tables show results in $ID_{50}$ values for inhibition of syncytia (concentration of an oligomer in micro grams/ml, it gives 50% inhibition under the assay condition) as an index.

The data from the tables describe favorable conclusions. The activity of the parent oligonucleotide, compound 1, is relatively low (ID50 less than 100). It appears that anchoring a cholesteryl fragment to the oligonucleotide significantly enhances the anti-HIV activity (from ID50 greater than 100 to 10). Thus, the cholestrol provides steriod means conjugated to the oligonucleotide for increasing the antiviral activity of the oligonucleotide. Further, anchoring a second cholesteryl fragment does not appear to be an improvement because the second cholesteryl leads to a reduction in activity relative to the monocholesteryl-oligonucleotide. It appears that a cholesteryl fragment to a phosphorothioate oligonucleotide analog enhances the antiviral property of the phosphorothioate derivative as shown in comparisons between compounds 6 and 7, 8 and 8, and 10 and 11. In the most favorable case, compound 7, the ID50 was reduced to 0.8 micrograms per milliter. With relatively large oligomers, those having 15 to 20-mers, the activity of the cholesteryl-oligonucleotides (natural phosphodiester links) appears to be independent of the chain link (compare compounds 2 and 5). A lack of dependence of activity on link has also been shown for unmodified oligonucleotides in the 15–20 mer range. Additionally, the activity of the cholesteryl modified phosphorothioate derivatives shows a downward trend as the length of the oligomer is decreased. Thus, the ID50 values increase from 0.8 for the 20-mer (compound 7) to about 3.5 for the 10–15 mers (compound 11 and 9), to 13 for the 6-mer (compound 14).

From Tables 2 and 3, it can also be concluded that the anti-HIV activity of the cholesteryl-modified oligonucleotides is not strongly dependent on the nucleotide sequence. This conclusion applies both to the phosphodiester and the phosphorothioate cholesteryl derivatives (compared to the data for compounds 2 and 3 has six mismatched base sites; and the data for compound 11 with that for compounds 12 and 13 which have 8 and 3 mismatched). For phosphorothioate derivatives, the activity of all three 10-mers is essentially the same although the sequence is different. Further, the cholesteryl modified oligomers are not toxic to cells even at concentrations far in excess of those that lead to complete inhibition of the replication of HIV. For all derivatives the LB50 was greater than 100 micrograms per ml.

TABLE 2

| | Inhibition of HIV by Oligonucleotides with Cholesteryl Substituents | | | |
|---|---|---|---|---|
| | conc. | % inhibition | | | ID$_{50}$ μg/ml |
| compound | μg/ml | syncytia | P24 | RT | (syncytia) |
| 1 (control) | 0.16 | 0 | | | >100 |
| | 0.8 | 3 | | | |
| | 4 | 20 | | | |
| | 20 | 34 | | | |
| | 100 | 45 | | | |
| 2 | 2 | 0 | 0 | | 10 |
| | 5 | 4 | 0 | 0 | |
| | 10 | 51 | 63 | 48 | |

TABLE 2-continued

Inhibition of HIV by Oligonucleotides with Cholesteryl Substituents

| compound | conc. μg/ml | % inhibition syncytia | P24 | RT | ID$_{50}$ μg/ml (syncytia) |
|---|---|---|---|---|---|
|   | 20 | 95 | 88 | 90 |   |
|   | 50 | 100 | 100 | 92 |   |
| 3 | 2 | 0 | 0 | 0 | 16 |
|   | 5 | 2 | 13 | 0 |   |
|   | 10 | 22 | 70 | 0 |   |
|   | 20 | 77 | 69 | 0 |   |
|   | 50 | 100 | 100 | 84 |   |
|   | 100 | 100 | 100 | 100 |   |
| 4 | 2 | 0 | 0 | 0 | 32 |
|   | 5 | 3 | 0 | 0 |   |
|   | 10 | 7 | 0 | 0 |   |
|   | 20 | 28 | 32 | 26 |   |
|   | 50 | 85 | 88 | 75 |   |
|   | 100 | 100 | 100 | 100 |   |
| 5 | 2 | 0 | 0 | 0 | 11 |
|   | 5 | 5 | 0 | 0 |   |
|   | 20 | 92 | 100 | 82 |   |
|   | 50 | 100 | 100 | 100 |   |
|   | 100 | 100 | 100 | 100 |   |

TABLE 3

Inhibition of HIV by Phosphorothioate Oligonucleotides with Cholesteryl Substituents

| compound | conc. μg/ml | % inhibition syncytia | P17 | P24 | RT | ID$_{50}$ μg/ml (syncytia) |
|---|---|---|---|---|---|---|
| 6 (phospho- diester control) | 2.5 | 15 | 18 | 22 | 33 | 6.0 |
|   | 6.25 | 56 | 67 | 81 | 70 |   |
|   | 10 | 90 | 89 | 89 | 85 |   |
|   | 25 | 100 | 100 | 100 | 100 |   |
| 7 | 0.25 | 0 | 12 | 19 | 23 | 0.8 |
|   | 1.0 | 74 | 69 | 70 | 68 |   |
|   | 1.5 | 100 | 100 | 100 | 100 |   |
|   | 6.0 | 100 | 100 | 100 | 100 |   |
| 8 (phospho- diester control) | 1.6 | 0 | 0 | 0 | 0 | 14.5 |
|   | 6.25 | 15 | 16 | 26 | 26 |   |
|   | 25 | 95 | 84 | 82 | 67 |   |
|   | 100 | 97 | 96 | 96 | 78 |   |
| 9 | 1.6 | 28 | 39 | 43 | 47 | 3.2 |
|   | 6.25 | 98 | 92 | 96 | 73 |   |
|   | 25 | 98 | 96 | 96 | 76 |   |
|   | 100 | 98 | 96 | 96 | 88 |   |
| 10 (phospho- diester | 1.6 | 0 | 0 | 0 | 0 | >100 |
|   | 6.25 | 0 | 4 | 4 | 0 |   |

TABLE 3-continued

Inhibition of HIV by Phosphorothioate Oligonucleotides with Cholesteryl Substituents

| compound | conc. μg/ml | % inhibition syncytia | P17 | P24 | RT | ID$_{50}$ (syncytia) |
|---|---|---|---|---|---|---|
| control) | 25 | 0 | 20 | 22 | 25 |   |
|   | 100 | 0 | 24 | 33 | 28 |   |
| 11 | 1.6 | 30 | 42 | 47 | 45 | 3.5 |
|   | 6.25 | 97 | 86 | 88 | 61 |   |
|   | 25 | 97 | 92 | 92 | 70 |   |
|   | 100 | 98 | 92 | 96 | 89 |   |
| 12 | 1.6 | 28 | 33 | 40 |   | 3.4 |
|   | 6.25 | 93 | 60 | 67 |   |   |
|   | 25 | 100 | 100 | 100 |   |   |
|   | 100 | 100 | 100 | 100 |   |   |
| 13 | 1.6 | 20 | 23 | 31 |   | 3.6 |
|   | 6.25 | 89 | 56 | 67 |   |   |
|   | 25 | 100 | 100 | 100 |   |   |
|   | 100 | 100 | 100 | 100 |   |   |
| 14 | 1.6 | 18 | 21 | 25 |   | 13 |
|   | 6.25 | 35 | 30 | 32 |   |   |
|   | 25 | 90 | 70 | 66 |   |   |
|   | 100 | 100 | 100 | 100 |   |   |
| 15 | 25 | 80 | 20 | 25 |   |   |
|   | 50 | 99 | 99 | 90 |   |   |
|   | 100 | 100 | 100 | 95 |   |   |

I claim:

1. An oligonucleotide comprising:

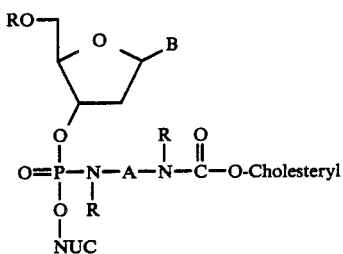

wherein A is selected from the group consisting of an aliphatic alkyl, branched aliphatic alkyl, and a heteroatom containing an alkyl chain of 2 to 18 carbon atoms, R is selected from the group consisting of H and lower alkyl up to 12 carbon atoms; NUC is selected from the group consisting of a phosphorothioate oligonucleotide and B is a base.

2. An oligonucleotide as set forth in claim 1 wherein said oligonucleotide includes 7 to 20 nucleotides.

3. The compound of claim 1 wherein A is $CH_2CH_2$.

* * * * *